US010499688B2

(12) United States Patent
Dickens

(10) Patent No.: US 10,499,688 B2
(45) Date of Patent: Dec. 10, 2019

(54) ELECTRONIC VAPOR PROVISION SYSTEM

(71) Applicant: Nicoventures Holdings Limited, London (GB)

(72) Inventor: Colin John Dickens, London (GB)

(73) Assignee: Nicoventures Holdings Limited, London (GB)

(*) Notice: Subject to any disclaimer, the term of this patent is extended or adjusted under 35 U.S.C. 154(b) by 0 days.

(21) Appl. No.: 15/317,854

(22) PCT Filed: Mar. 30, 2015

(86) PCT No.: PCT/GB2015/050958
§ 371 (c)(1),
(2) Date: Dec. 9, 2016

(87) PCT Pub. No.: WO2015/189556
PCT Pub. Date: Dec. 17, 2015

(65) Prior Publication Data
US 2017/0135401 A1 May 18, 2017

(30) Foreign Application Priority Data
Jun. 9, 2014 (GB) .................................. 1410171.1

(51) Int. Cl.
*A24F 47/00* (2006.01)
*A61M 15/06* (2006.01)
(Continued)

(52) U.S. Cl.
CPC ......... *A24F 47/008* (2013.01); *A61M 11/042* (2014.02); *A61M 15/06* (2013.01);
(Continued)

(58) Field of Classification Search
CPC ..... A24F 47/008; A61M 11/042; A61M 15/06
See application file for complete search history.

(56) References Cited

U.S. PATENT DOCUMENTS 4,922,901 A  5/1990 Brooks et al.
4,974,874 A  12/1990 Muraoka
(Continued)

FOREIGN PATENT DOCUMENTS

CN  203575649 U  5/2014
CN  203676125 U  7/2014
(Continued)

OTHER PUBLICATIONS

International Search Report for corresponding International Application No. PCT/GB2015/050958 dated Jun. 12, 2015; 7 pages.
(Continued)

*Primary Examiner* — Tulsidas C Patel
*Assistant Examiner* — Marcus E Harcum
(74) *Attorney, Agent, or Firm* — Patterson Thuente Pedersen, P.A.

(57) ABSTRACT

An electronic vapor provision system includes a vaporizer for vaporizing liquid for inhalation by a user of the electronic vapor provision system; a power supply comprising a cell or battery for supplying power to the vaporizer; a sensor for measuring the rate of airflow through the electronic vapor provision system as a result of the inhalation by the user; and a control unit for controlling the power supplied to the vaporizer based on a cumulative airflow for this inhalation by the user, wherein the cumulative airflow is determined based on the measurements of airflow rate by the sensor. Such a system allows the user control over the amount of vaporized liquid obtained in a given inhalation based on the cumulative airflow for the given inhalation.

14 Claims, 4 Drawing Sheets

(51) Int. Cl.
*A61M 11/04* (2006.01)
*H05B 1/02* (2006.01)
*A61M 16/00* (2006.01)

(52) U.S. Cl.
CPC ... *H05B 1/0244* (2013.01); *A61M 2016/0024* (2013.01); *A61M 2016/0039* (2013.01); *A61M 2205/3372* (2013.01); *A61M 2205/8206* (2013.01)

(56) References Cited

U.S. PATENT DOCUMENTS

| | | | |
|---|---|---|---|
| 5,894,841 | A | 4/1999 | Voges |
| 6,196,218 | B1 | 3/2001 | Voges |
| 9,609,894 | B2 | 4/2017 | Abramov |
| 2004/0084044 | A1 | 5/2004 | Childers et al. |
| 2007/0240712 | A1 | 10/2007 | Fleming et al. |
| 2011/0226236 | A1 | 9/2011 | Buchberger |
| 2011/0265806 | A1 | 11/2011 | Alarcon et al. |
| 2012/0048266 | A1 | 3/2012 | Alelov |
| 2012/0291791 | A1 | 11/2012 | Pradeep |
| 2013/0192623 | A1* | 8/2013 | Tucker ............... H01C 17/00 131/329 |
| 2013/0220315 | A1* | 8/2013 | Conley ............... A24F 47/008 128/202.21 |
| 2013/0255702 | A1 | 10/2013 | Griffith, Jr. et al. |
| 2013/0276799 | A1 | 10/2013 | Davidson et al. |
| 2013/0284194 | A1 | 10/2013 | Newton |
| 2014/0182608 | A1 | 7/2014 | Egoyants |
| 2014/0202476 | A1 | 7/2014 | Egoyants |
| 2014/0360515 | A1 | 12/2014 | Vasiliev |
| 2015/0027467 | A1 | 1/2015 | Liu |
| 2015/0173419 | A1* | 6/2015 | Tu ..................... A24F 47/008 131/329 |
| 2015/0196057 | A1* | 7/2015 | Wu ..................... A24F 47/008 131/329 |
| 2016/0255879 | A1 | 9/2016 | Paprocki |
| 2016/0278435 | A1* | 9/2016 | Choukroun ........... A24F 47/008 |
| 2017/0156406 | A1 | 6/2017 | Abramov |
| 2017/0156407 | A1 | 6/2017 | Abramov |

FOREIGN PATENT DOCUMENTS

| | | |
|---|---|---|
| DE | 10 2007 011 120 A1 | 9/2008 |
| EP | 1 618 803 A1 | 1/2006 |
| EP | 2 113 178 A1 | 11/2009 |
| EP | 2 460 423 A1 | 6/2012 |
| WO | WO 2010/145805 A1 | 12/2010 |
| WO | WO 2012/109371 A2 | 8/2012 |
| WO | WO 2013/040193 A2 | 3/2013 |
| WO | WO 2013/060781 A1 | 5/2013 |
| WO | WO 2013/060784 A2 | 5/2013 |
| WO | WO 2014/054035 A1 | 4/2014 |
| WO | WO2012085207 | 6/2018 |

OTHER PUBLICATIONS

Written Opinion of the International Searching Authority for corresponding International Application No. PCT/GB2015/050958 dated Jun. 12, 2015; 8 pages.

International Preliminary Report on Patentability for corresponding International Application No. PCT/GB2015/050958 dated Aug. 19, 2016; 26 pages.

Korean Office Action, Application No. 10-2016-7034484, dated Mar. 21, 2018, 8 pages (15 pages with translation).

Chinese Office Action, Application No. 201580030768.6, dated Jul. 18, 2018, 8 pages (19 pages with translation).

* cited by examiner

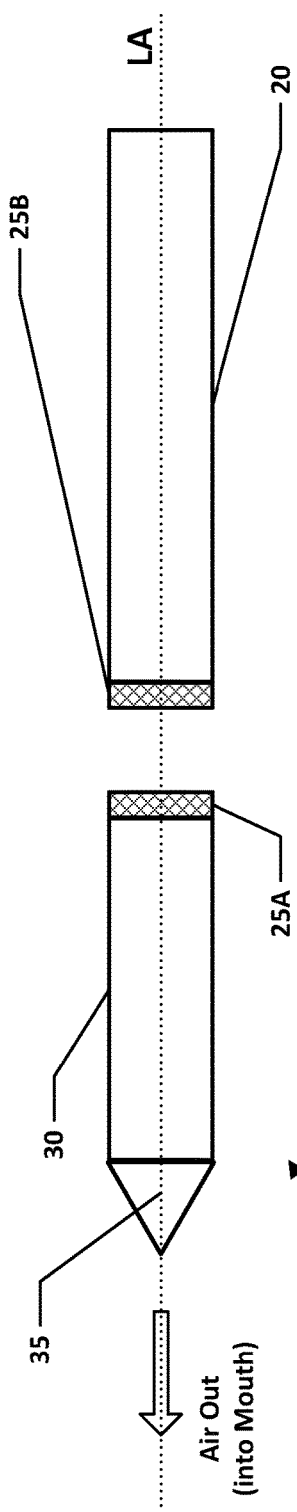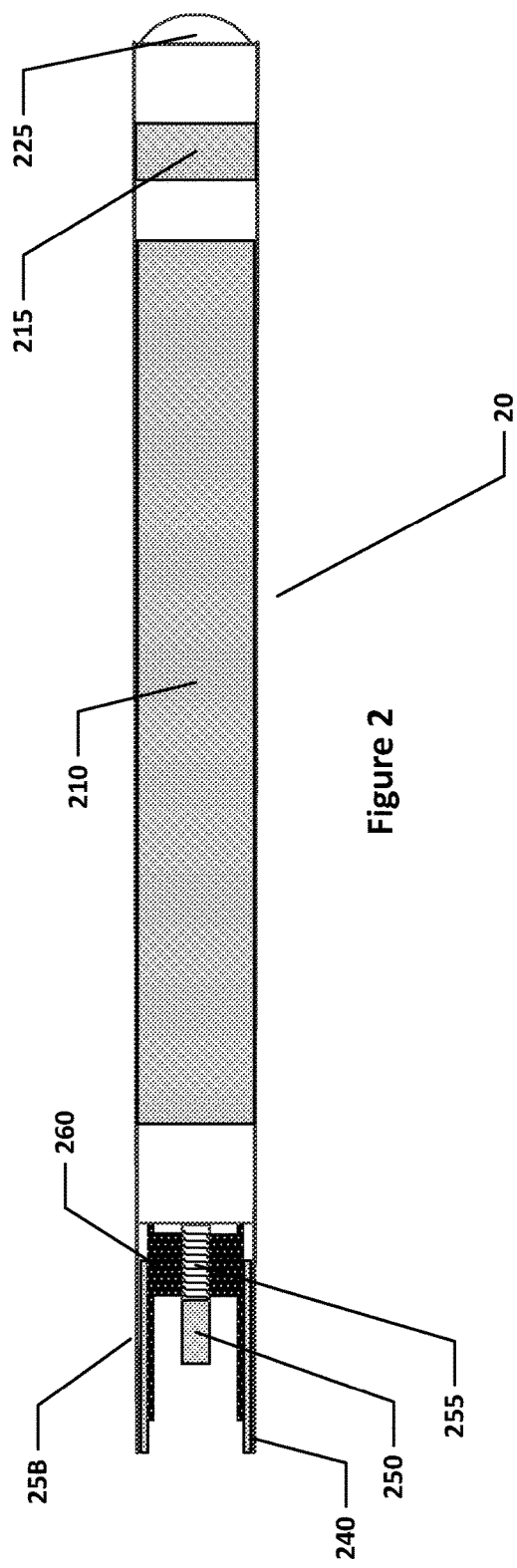

ELECTRONIC VAPOR PROVISION SYSTEM

CROSS-REFERENCE TO RELATED APPLICATIONS

The present application is a National Phase entry of PCT Application No. PCT/GB2015/050958, filed on 30 Mar. 2015, which claims priority to GB Patent Application No. 1410171.1, filed on 9 Jun. 2014, which are hereby fully incorporated herein by reference.

TECHNICAL FIELD

The present disclosure relates to electronic vapor provision systems such as electronic nicotine delivery systems (e.g. e-cigarettes).

BACKGROUND

Electronic vapor provision systems such as e-cigarettes generally contain a reservoir of liquid, typically nicotine, which is to be vaporized or otherwise converted into an aerosol. For example, when a user inhales on the device, a heater is activated to vaporize a small amount of liquid, which is therefore inhaled by the user. More particularly, such devices are usually provided with one or more air inlet holes located away from the mouthpiece. When a user sucks on the mouthpiece, air is drawn in through the inlet holes and past the vapor source, such as the heater supplied with nicotine or other liquid from a cartridge.

The amount of power provided to the heater may be controlled for operational reasons. For example, WO 2012/109371 describes a device which has different operating modes, and the selection of operating mode depends on the interval between successive puffs (since for a short interval, the heater may already be warm from a previous puff). WO 2013/060784 describes a device which reduces the power supplied to the heater towards the end of an inhalation in order to reduce unwanted condensation of aerosol within the device.

In some known devices, the user can exercise a certain degree of control over the operation of an electronic vapor provision system. Such control may, for example, allow a user to alter the power delivered to the heater by rotating a dial. However, existing mechanisms for controlling a user experience are still somewhat limited in terms of flexibility, responsiveness and ease of use.

SUMMARY

An electronic vapor provision system includes a vaporizer for vaporizing liquid for inhalation by a user of the electronic vapor provision system; a power supply comprising a cell or battery for supplying power to the vaporizer; a sensor for measuring the rate of airflow through the electronic vapor provision system as a result of the inhalation by the user; and a control unit for controlling the power supplied to the vaporizer based on a cumulative airflow for this inhalation by the user, wherein the cumulative airflow is determined based on the measurements of airflow rate by the sensor. Such a system allows the user control over the amount of vaporized liquid obtained in a given inhalation based on the cumulative airflow for the given inhalation.

The approach described herein is not restricted to specific embodiments such as set out below, but includes and contemplates any appropriate combinations of features presented herein. For example, an electronic vapor provision system may be provided in accordance with the approach described herein which includes any one or more of the various features described below as appropriate.

BRIEF DESCRIPTION OF THE DRAWINGS

Various embodiments of the disclosure will now be described in detail by way of example only with reference to the following drawings:

FIG. 1 is a schematic (exploded) diagram of an electronic vapor provision system such as an e-cigarette in accordance with some embodiments of the disclosure.

FIG. 2 is a schematic diagram of the body of the e-cigarette of FIG. 1 in accordance with some embodiments of the disclosure.

DETAILED DESCRIPTION

Figure 3:
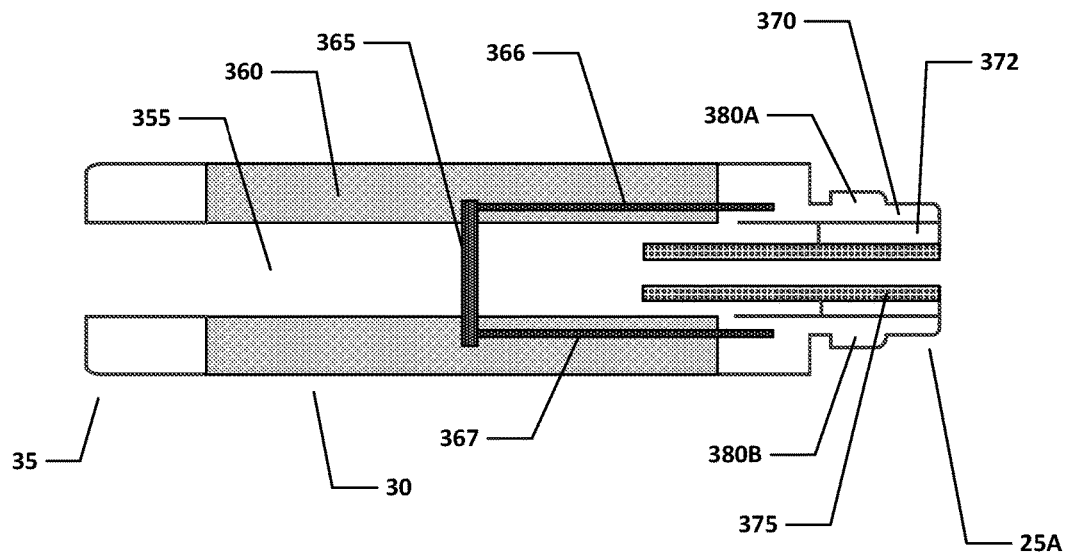
FIG. 3 is a schematic diagram of the vaporizer portion of the e-cigarette of FIG. 1 in accordance with some embodiments of the disclosure.

As described above, the present disclosure relates to an electronic vapor provision system, such as an e-cigarette. Throughout the following description the term "e-cigarette" is used; however, this term may be used interchangeably with electronic vapor provision system.

FIG. 1 is a schematic diagram of an electronic vapor provision system such as an e-cigarette 10 in accordance with some embodiments of the disclosure (not to scale). The e-cigarette has a generally cylindrical shape, extending along a longitudinal axis indicated by dashed line LA, and comprises two main components, namely a body 20 and a cartomizer 30. The cartomizer includes an internal chamber containing a reservoir of nicotine, a vaporizer (such as a heater), and a mouthpiece 35. The reservoir may be a foam matrix or any other structure for retaining the nicotine until such time that it is required to be delivered to the vaporizer. The cartomizer 30 also includes a heater for vaporizing the nicotine and may further include a wick or similar facility to transport a small amount of nicotine from the reservoir to a heating location on or adjacent the heater.

The body 20 includes a re-chargeable cell or battery to provide power to the e-cigarette 10 and a circuit board for generally controlling the e-cigarette. When the heater receives power from the battery, as controlled by the circuit board, the heater vaporizes the nicotine and this vapor is then inhaled by a user through the mouthpiece.

The body 20 and cartomizer 30 are detachable from one another by separating in a direction parallel to the longitudinal axis LA, as shown in FIG. 1, but are joined together when the device 10 is in use by a connection, indicated schematically in FIG. 1 as 25A and 25B, to provide mechanical and electrical connectivity between the body 20 and the cartomizer 30. The electrical connector on the body 20 that is used to connect to the cartomizer also serves as a socket for connecting a charging device (not shown) when the body is detached from the cartomizer 30. The other end of the charging device can be plugged into a USB socket to re-charge the cell in the body of the e-cigarette. In other implementations, a cable may be provided for direct connection between the electrical connector on the body and a USB socket.

The e-cigarette 10 is provided with one or more holes (not shown in FIG. 1) for air inlet. These holes connect to an air passage through the e-cigarette 10 to the mouthpiece 35. When a user inhales through the mouthpiece 35, air is drawn into this air passage through the one or more air inlet holes, which are suitably located on the outside of the e-cigarette. This airflow (or the resulting change in pressure) is detected by a pressure sensor that in turn activates the heater to vaporize the nicotine from the cartridge. The airflow passes through, and combines with, the nicotine vapor, and this combination of airflow and nicotine vapor then passes out of the mouthpiece 35 to be inhaled by a user. The cartomizer 30 may be detached from the body 20 and disposed of when the supply of nicotine is exhausted (and replaced with another cartomizer if so desired).

It will be appreciated that the e-cigarette 10 shown in FIG. 1 is presented by way of example, and various other implementations can be adopted. For example, in some embodiments, the cartomizer 30 is provided as two separable components, namely a cartridge comprising the nicotine reservoir and mouthpiece (which can be replaced when the nicotine from the reservoir is exhausted), and a vaporizer comprising a heater (which is generally retained). As another example, the charging facility may connect to an additional or alternative power source, such as a car cigarette lighter.

FIG. 2 is a schematic (simplified) diagram of the body 20 of the e-cigarette of FIG. 1 in accordance with some embodiments of the disclosure. FIG. 2 can generally be regarded as a cross-section in a plane through the longitudinal axis LA of the e-cigarette. Note that various components and details of the body, e.g. such as wiring and more complex shaping, have been omitted from FIG. 2 for reasons of clarity.

As shown in FIG. 2, the body 20 includes a battery or cell 210 for powering the e-cigarette 10, as well as a chip, such as an application specific integrated circuit (ASIC) or microcontroller for controlling the e-cigarette 10. The ASIC may be positioned alongside or at one end of the battery 210. The ASIC is attached to a sensor unit 215 to detect an inhalation on mouthpiece 35 (or alternatively the sensor unit 215 may be provided on the ASIC itself). In response to such a detection, the ASIC provides power from the battery or cell 210 to a heater in the cartomizer 30 to vaporize nicotine into the airflow which is inhaled by a user.

The body further includes a cap 225 to seal and protect the far (distal) end of the e-cigarette. There is an air inlet hole provided in or adjacent to the cap 225 to allow air to enter the body and flow past the sensor unit 215 when a user inhales on the mouthpiece 35. This airflow therefore allows the sensor unit 215 to detect the user inhalation.

At the opposite end of the body 20 from the cap 225 is the connector 25B for joining the body 20 to the cartomizer 30. The connector 25B provides mechanical and electrical connectivity between the body 20 and the cartomizer 30. The connector 25B includes a body connector 240, which is metallic (silver-plated in some embodiments) to serve as one terminal for electrical connection (positive or negative) to the cartomizer 30. The connector 25B further includes an electrical contact 250 to provide a second terminal for electrical connection to the cartomizer 30 of opposite polarity to the first terminal, namely body connector 240. The electrical contact 250 is mounted on a coil spring 255. When the body 20 is attached to the cartomizer 30, the connector 25A on the cartomizer 30 pushes against the electrical contact 250 in such a manner as to compress the coil spring in an axial direction, i.e. in a direction parallel to (co-aligned with) the longitudinal axis LA. In view of the resilient nature of the spring 255, this compression biases the spring 255 to expand, which has the effect of pushing the electrical contact 250 firmly against connector 25A, thereby helping to ensure good electrical connectivity between the body 20 and the cartomizer 30. The body connector 240 and the electrical contact 250 are separated by a trestle 260, which is made of a non-conductor (such as plastic) to provide good insulation between the two electrical terminals. The trestle 260 is shaped to assist with the mutual mechanical engagement of connectors 25A and 25B.

FIG. 3 is a schematic diagram of the cartomizer 30 of the e-cigarette of FIG. 1 in accordance with some embodiments of the disclosure. FIG. 3 can generally be regarded as a cross-section in a plane through the longitudinal axis LA of the e-cigarette. Note that various components and details of the body, e.g. such as wiring and more complex shaping, have been omitted from FIG. 3 for reasons of clarity.

The cartomizer 30 includes an air passage 355 extending along the central (longitudinal) axis of the cartomizer 30 from the mouthpiece 35 to the connector 25A for joining the cartomizer 30 to the body 20. A reservoir of nicotine 360 is provided around the air passage 335. This reservoir 360 may be implemented, for example, by providing cotton or foam soaked in nicotine. The cartomizer 30 also includes a heater 365 for heating nicotine from reservoir 360 to generate nicotine vapor to flow through air passage 355 and out through mouthpiece 35 in response to a user inhaling on the e-cigarette 10. The heater 365 is powered through lines 366 and 367, which are in turn connected to opposing polarities (positive and negative, or vice versa) of the battery 210 via connector 25A (the details of the wiring between the power lines 366 and 367 and connector 25A are omitted from FIG. 3).

The connector 25A includes an inner electrode 375, which may be silver-plated or made of some other suitable metal. When the cartomizer 30 is connected to the body 20, the inner electrode 375 contacts the electrical contact 250 of the body 20 to provide a first electrical path between the cartomizer 30 and the body. In particular, as the connectors 25A and 25B are engaged, the inner electrode 375 pushes against the electrical contact 250 so as to compress the coil spring 255, thereby helping to ensure good electrical contact between the inner electrode 375 and the electrical contact 250.

The inner electrode 375 is surrounded by an insulating ring 372, which may be made of plastic, rubber, silicone, or any other suitable material. The insulating ring 372 is surrounded by the cartomizer connector 370, which may be silver-plated or made of some other suitable metal or conducting material. When the cartomizer 30 is connected to the body 20, the cartomizer connector 370 contacts the body connector 240 of the body 20 to provide a second electrical path between the cartomizer 30 and the body 20. In other words, the inner electrode 375 and the cartomizer connector 370 serve as positive and negative terminals (or vice versa) for supplying power from the battery 210 in the body to the heater 365 in the cartomizer 30 via supply lines 366 and 367 as appropriate.

The cartomizer connector 370 is provided with two lugs or tabs 380A, 380B, which extend in opposite directions away from the longitudinal axis of the e-cigarette. These tabs are used to provide a bayonet fitting in conjunction with the body connector 240 for connecting the cartomizer 30 to the body 20. This bayonet fitting provides a secure and robust connection between the cartomizer 30 and the body 20, so that the cartomizer 30 and body 20 are held in a fixed position relative to one another, without wobble or flexing, and the likelihood of any accidental disconnection is very small. At the same time, the bayonet fitting provides simple and rapid connection and disconnection by an insertion followed by a rotation for connection, and a rotation (in the reverse direction) followed by withdrawal for disconnection. It will be appreciated that other embodiments may use a different form of connection between the body 20 and the cartomizer 30, such as a snap fit or a screw connection.

Figure 4:
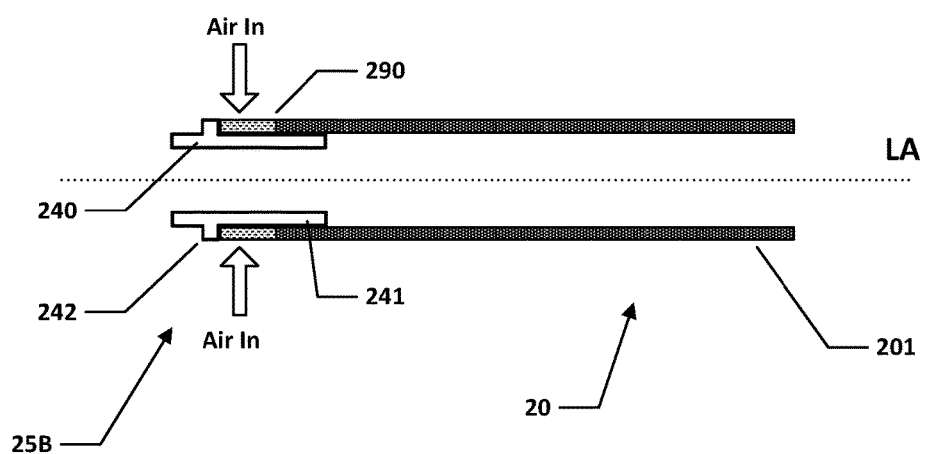
FIG. 4 is a schematic diagram showing certain aspects of one end of the body portion of the e-cigarette of FIG. 1 in accordance with some embodiments of the disclosure.

FIG. 4 is a schematic diagram of certain details of the connector 25B at the end of the body 20 in accordance with some embodiments of the disclosure (but omitting for clarity most of the internal structure of the connector as shown in FIG. 2, such as trestle 260). In particular, FIG. 4 shows the external housing 201 of the body 20, which generally has the form of a cylindrical tube. This external housing 201 may comprise, for example, an inner tube of metal with an outer covering of paper or similar.

The body connector 240 extends from this external housing 201 of the body 20. The body connector as shown in FIG. 4 comprises two main portions, a shaft portion 241 in the shape of a hollow cylindrical tube, which is sized to fit just inside the external housing 201 of the body 20, and a lip portion 242 which is directed in a radially outward direction, away from the main longitudinal axis (LA) of the e-cigarette. Surrounding the shaft portion 241 of the body connector 240, where the shaft portion does not overlap with the external housing 201, is a collar or sleeve 290, which is again in a shape of a cylindrical tube. The collar 290 is retained between the lip portion 242 of the body connector 240 and the external housing 201 of the body 20, which together prevent movement of the collar 290 in an axial direction (i.e. parallel to axis LA). However, collar 290 is free to rotate around the shaft portion 241 (and hence also axis LA).

As mentioned above, the cap 225 is provided with an air inlet hole to allow air to flow past sensor 215 when a user inhales on the mouthpiece 35. However, the majority of air that enters the device when a user inhales flows through collar 290 and body connector 240 as indicated by the two arrows in FIG. 4.

Figure 5:
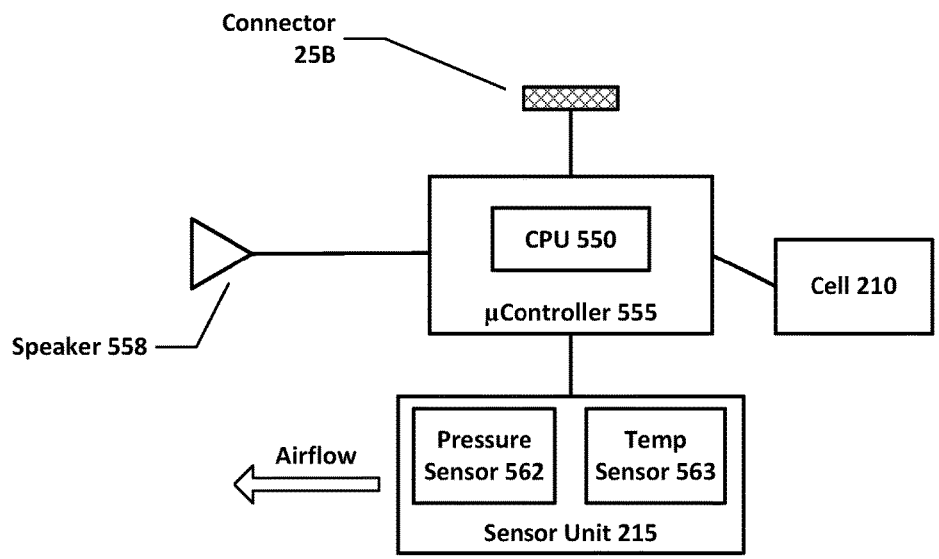
FIG. 5 is a schematic diagram of the main functional components of the body of the e-cigarette of FIG. 1 in accordance with some embodiments of the disclosure.

FIG. 5 is a schematic diagram of the main functional components of the body 20 of the e-cigarette 10 of FIG. 1 in accordance with some embodiments of the disclosure. These components may be mounted on the circuit board provided within the body 20, although depending on the particular configuration, in some embodiments, one or more of the components may instead be accommodated in the body 20 to operate in conjunction with the circuit board, but is/are not physically mounted on the circuit board itself.

The body 20 includes the sensor unit 215 located in or adjacent to the air path through the body 20 from the air inlet to the air outlet (to the vaporizer). The sensor unit 215 includes a pressure drop sensor 562 and temperature sensor 563 (also in or adjacent to this air path). The body 20 further includes a small speaker 558 and an electrical socket or connector 5B for connecting to the cartomizer 30 or to a USB charging device.

The microcontroller (e.g. an ASIC) 555 includes a CPU 550. The operations of the CPU 550 and other electronic components, such as the pressure sensor 562, are generally controlled at least in part by software programs running on the CPU 550 (or other component). Such software programs may be stored in non-volatile memory, such as ROM, which can be integrated into the microcontroller 555 itself, or provided as a separate component. The CPU 550 may access the ROM to load and execute individual software programs as and when required. The microcontroller 555 also contains appropriate communications interfaces (and control software) for communicating as appropriate with other devices in the body 20, such as the pressure sensor 562.

The CPU 550 controls the speaker 558 to produce audio output to reflect conditions or states within the e-cigarette 10, such as a low battery warning. Different signals for signaling different states or conditions may be provided by utilizing tones or beeps of different pitch and/or duration, and/or by providing multiple such beeps or tones.

As noted above, the e-cigarette 10 provides an air path from the air inlet through the e-cigarette 10, past the pressure drop sensor 562 and the heater (in the vaporizer or cartomizer 30), to the mouthpiece 35. Thus when a user inhales on the mouthpiece of the e-cigarette 10, the CPU 550 detects such inhalation based on information from the pressure drop sensor. In response to such a detection, the CPU 550 supplies power from the battery or cell 210 to the heater, which thereby heats and vaporizes the nicotine from the wick for inhalation by the user.

The e-cigarette 10 is configured to respond to a puff (inhalation) from a user or consumer, such that the amount and/or quality of the vapor generated is controllable by the consumer based on the puff effort and/or puff volume. This is somewhat similar to the situation with a conventional combustible cigarette, which responds to a consumer's puff with total particulate matter (TPM) being roughly proportional to puff volume (for a particular cigarette type). Accordingly, the puff effort or cumulative puff volume for a given inhalation is measured in the e-cigarette 10 using sensor unit 215, and the microcontroller 555 is configured so that e-cigarette 10 responds to the measured puff volume or effort by delivering more/less vapor (as appropriate) and/or a different quality of vapor. This gives a consumer an intuitive way to control their use of the e-cigarette 10 in terms of vapor production, etc.

Figure 6:
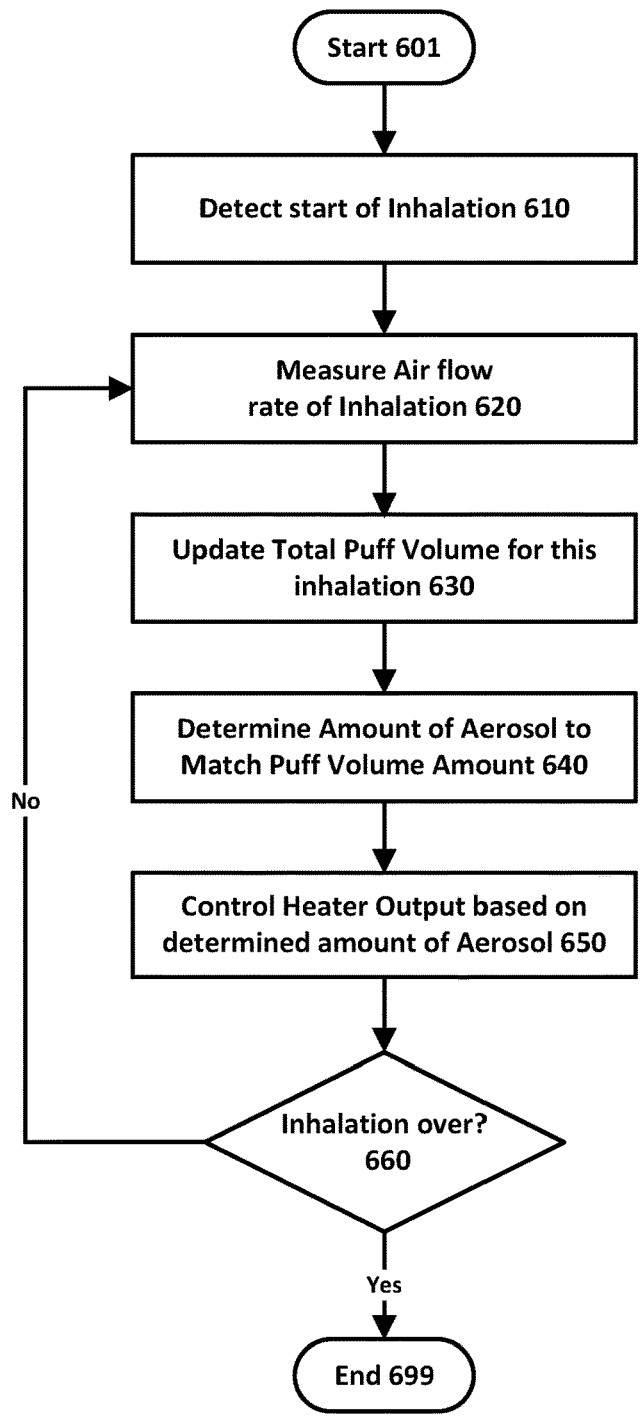
FIG. 6 is a schematic flowchart which illustrates certain aspects of operation of the e-cigarette of FIG. 1 in accordance with some embodiments of the disclosure.

FIG. 6 is a schematic flowchart which illustrates certain aspects of operation of the e-cigarette of FIG. 1 in accordance with some embodiments of the invention to provide such user control based on puff volume or effort. Processing commences with the detection of the start of a user inhalation (puff) at operation 610. Such a detection is made by sensor unit 215, in particular, pressure sensor 562, which detects the drop in pressure caused by the user sucking on the mouthpiece 35. In addition, using the measured pressure drop, once an inhalation has been detected, the airflow rate through the e-cigarette can be determined (operation 620). A more accurate determination can generally be made if the temperature of the airflow is also included (since the density of air is temperature dependent). Therefore, such a temperature may be measured at the same time as the pressure drop (such as by using the temperature sensor 563 included in sensor unit 215, see FIG. 5) and this measured temperature can be incorporated into the determination of the airflow. If the sensor unit does not include a temperature sensor, then a fixed (average) temperature may be assumed.

The relationship between pressure drop and airflow rate (and temperature, if available) may be determined empirically and/or by calculation/modeling. In the former case, the e-cigarette 10 can be placed in a mechanical device that simulates inhalation through the mouthpiece. This then allows measurements of airflow through the mouthpiece against pressure drop (as determined by the pressure sensor 562), including temperature sensitivity if so desired, thereby allowing an empirical relationship between the two to be developed. Alternatively, the relationship between pressure drop and airflow rate may be modeled based on the known internal shape of the e-cigarette, using fluid dynamics, etc. The resulting relationship between pressure drop and airflow rate (and temperature, if available), whether determined empirically or by calculation/modeling (or by a combination of the two) can then be provided to the microcontroller 555, either as code implementing a suitable mathematical expression corresponding to the relationship, or as suitable set of data values, e.g. in the form of a lookup table stored in some ROM in, or at least accessible to, the microcontroller 555. This relationship allows the microcontroller 555 to determine the current airflow rate based on the measured pressure drop from pressure sensor 562.

In other implementations, the sensor unit 215 may include an airflow monitor to directly measure airflow (rather than pressure drop). In such implementations, it may still be desirable to determine empirically and/or by calculation/modeling the relationship between the airflow measured by this monitor and the actual volume inhaled by a user.

Having measured and determined the current airflow at operation 620, the total or cumulative airflow for this puff or inhalation is now determined (operation 630). This cumulative airflow can be determined in effect by summing or integrating the current (instantaneous) airflow as measured at operation 620 for the duration of the inhalation (so far).

The e-cigarette 10 now uses the cumulative inhalation volume so far for this particular puff to control the vapor output in this same puff (operation 640). In other words, the e-cigarette supports an adaptive, real-time control facility for modifying the vapor output to the user through the mouthpiece 35. This control may be exercised in a variety of ways, for example:

delivering an amount of aerosol (vapor) which is proportional to cumulative airflow
  delivering an amount of aerosol (vapor) which is proportional to some other, e.g. non-linear, function of cumulative airflow, such as following an exponential or logarithmic relationship
  adjusting a mix of flavors with the aerosol (vapor) based on cumulative airflow.
  adjusting a particle size within the aerosol (vapor) based on cumulative airflow.

The above possibilities are provided by way of example only, and further ways for controlling the vapor output of the e-cigarette 10 in accordance with the cumulative airflow volume (so far) will be apparent to the skilled person.

The microcontroller 555 is generally responsible for implementing the desired control of vapor output based on the measured cumulative airflow for the current puff. For example, the microcontroller 555 may increase (or decrease) the power supplied to the heater 365 in order to increase (or decrease) the production rate of vapor or aerosol. In some implementations, such power control may be implemented by altering the current (and/or voltage) supplied to the heater 365. Other embodiments may use a different approach, such as pulse width modulation (PWM). In the PWM, a pulse of electrical power is delivered to the heater every time period or window Tw, where Tw is selected to be relatively short, so that the heater does not change significantly in temperature during the interval Tw (without receiving any power). The duration of the pulse itself, Tp, is selected to occupy a fraction (or potentially all) of the time window, i.e. Tw≥Tp.

The amount of power provided (on average) to the heater can be controlled by adjusting Tp, with the maximum provision of power occurring when Tp=Tw.

In some implementations, the heater 365 may comprise multiple different elements which can be separately controlled, with different flavors vaporized by different heater elements. This then allows the microcontroller to alter the mix of flavors within the output from the e-cigarette by varying the power supplied to the different heater elements according to the desired mix of flavors.

The processing of FIG. 6 now makes a determination as to whether or not the inhalation is over (operation 660)—this can be detected by the absence of any pressure drop across the pressure sensor unit 562. If the inhalation is over, this represents the end of the processing for this particular puff. Alternatively, if a pressure drop is still detected, hence the inhalation is still ongoing, the processing cycles back to operation 620. The e-cigarette 10 then measures again the airflow of the inhalation and uses this measurement to update the cumulative puff volume so far (operation 630). This then allows the determination of the aerosol amount and the heater control to be updated accordingly at operations 640 and 650 respectively. This processing loop then continues as before until the inhalation is finally over, as detected at operation 660.

Figure 7:
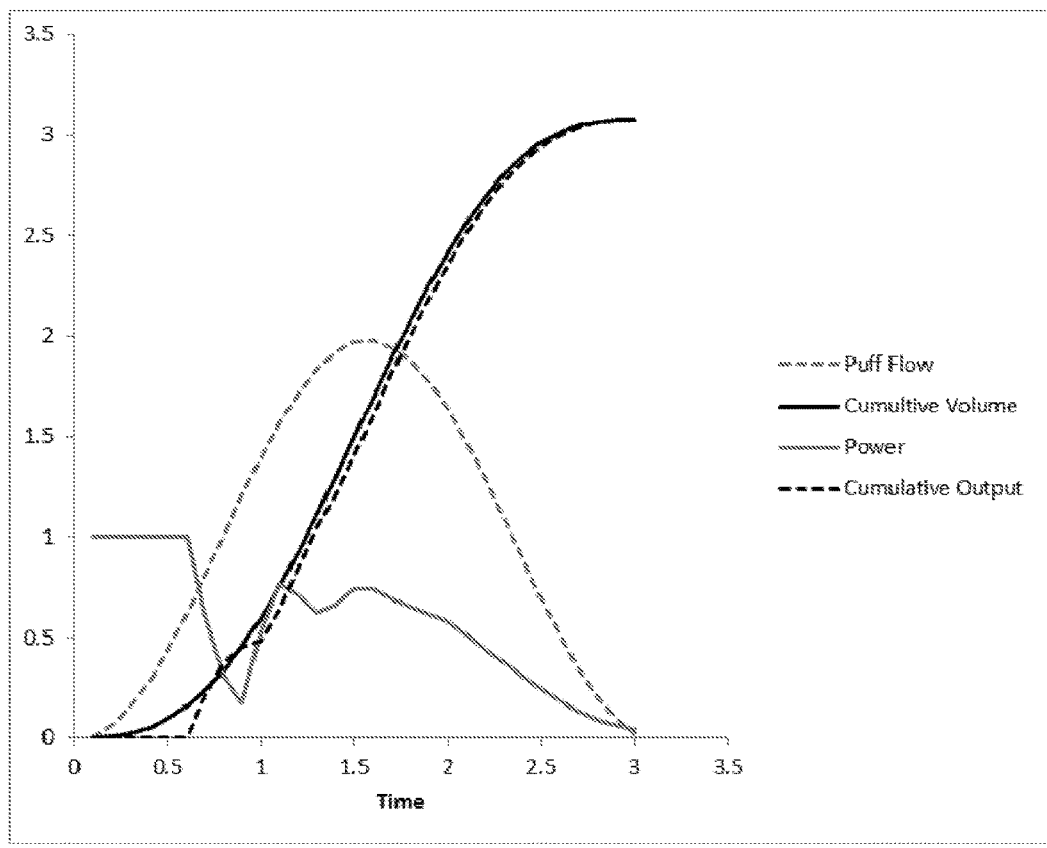
FIG. 7 is a graph showing some results corresponding to the approach shown in FIG. 6 in accordance with some embodiments of the disclosure.

FIG. 7 is a graph showing an example of controlling the power to a heater 365 with a view to delivering a cumulative amount of aerosol that matches (corresponds to) the cumulative puff volume using a linear (proportionality) relationship in the course of a single inhalation. There are four lines plotted in FIG. 7 which are as follows:

a) puff flow—i.e. current rate of airflow being inhaled by the user (light, dashed line)
  b) cumulative airflow—in effect, the integral of (a), representing the total amount of airflow for this puff (dark, solid line)
  c) power supplied to the heater—(light, solid line)
  d) cumulative output of vapor, in effect, the total volume of vapor output so far this puff.

The X-axis of FIG. 7 is time (seconds), while the scale of the Y-axis represents the power level supplied to the heater as a function of the maximum available power supply to the heater—i.e. as per line (c) above. (The scaling on the Y-axis for the other three lines depicted in FIG. 7 is arbitrary.)

The amount of aerosol or vapor delivered by the e-cigarette is dependent on various factors, especially the power delivered to the heater 365, expected temperature of the heater 365 (which is itself related to the power delivered to the heater 365), expected temperature loss from the heater 365 due to convention & radiation, and temperature loss due to evaporation of the formulation, i.e. the nicotine or other liquid to be vaporized. The aerosol delivered is generally proportional to the temperature loss due to formulation evaporation.

As shown in FIG. 7, when a puff is detected (corresponding to operation 610 in FIG. 6), the power to the heater 365 is set initially to 100% to bring the e-cigarette 10 up to an active temperature (as per line (c)). At this stage, the puff airflow (line (a)) is increasing steadily. This reflects the motion of the lungs of the user, which have to be accelerated from an initial rest position. As the lungs accelerate to greater speed, so the airflow of the inhalation increases.

In the particular example of FIG. 7, the microcontroller 555 is tasked with having the cumulative vapor output match (track) the cumulative airflow output. It will be appreciated that this leads to an approximately constant proportion of vapor within the airflow—so that when the user inhales most strongly to produce the greatest airflow, the amount of vapor inhaled (in absolute terms) is likewise at a maximum.

At the beginning, the cumulative puff airflow (line (b)) goes ahead of the cumulative vapor output (line (d)), because of the delay in producing vapor while the heater temperature is raised to its operational point. Once this has occurred, after about 0.5 seconds in FIG. 7, vapor starts being produced. At this point, the vapor output, and hence the cumulative vapor output (line (d)), rise rapidly, in effect catching up with the cumulative airflow (line (b)).

The power to the heater 365 now drops to avoid overheating. However, as the airflow past the heater 365 increases (as indicated by line (a)), this allows the heater 365 to vaporize more liquid (since the increased airflow draws the previously vaporized liquid out of the e-cigarette 10). This then leads to increased power requirements for the heater 365, and hence a rise in the power supply to the heater 365 just before 1 s.

Over the next second, the rate of increase in the airflow (line (a)) starts to decrease, and then eventually the airflow rate itself peaks and starts to fall. The heater power (line (c)) likewise peaks and then starts to fall in this period. Finally, in the last second of the inhalation (from 2 s to 3 s), the airflow rate of the inhalation steadily declines back down to zero, and again the heater power (line (c)) shows a generally similar decrease.

In terms of control theory, we can represent the rate of vapor output as V(t) and the power input to the heater as P(t), such that V(t)=H(P(t)), where H is a transfer function based on factors discussed above, such as previously supplied power to the heater, loss of heat from the heater due to vapor production, etc. If the measured airflow rate is A(t), then the overall objective for the microcontroller is that F1(V(t))=F2(A(t)), where F1 and F2 are functions to be specified and may include a timing offset between the measured airflow (input) rate and the vapor output. Taking the example of FIG. 7, this corresponds to having F1 and F2 such that:

$$\int_0^t V(t) = k \int_0^t A(t)$$

where k is a constant, and the puff is assumed to start at t=0, so that the left hand side represents the cumulative vapor output for this puff, while the right hand side represents the cumulative airflow into (and through) the system for this puff.

Writing $H^{-1}$ as the inverse of H, and $F3=F1^{-1}(F2)$, where $F^{-1}$ is likewise the inverse of F, then $V(t)=F3(A(t))$, and $P(t)=H^{-1}(V(0))$, and we therefore have $P(t)=H^{-1}(F3(A(0)))$. It will be appreciated that this equation can be used by the microcontroller 555 to determine the power input to the heater based on (i) the measured airflow rate A(t), (ii) the desired relationship between the airflow rate and the vapor output rate V(t), as represented by the function F3, and (iii) the relationship between the power input to the heater 365 and the vapor output rate, as represented by the transfer function H (and its inverse $H^{-1}$).

As described herein, various embodiments provide an electronic vapor provision system including a vaporizer for vaporizing liquid for inhalation by a user of the electronic vapor provision system, a power supply comprising a cell or battery for supplying power to the vaporizer; a sensor for measuring the rate of airflow through the electronic vapor provision system as a result of the inhalation by the user; and a control unit. The control unit controls the power supplied to the vaporizer based on a cumulative airflow for this inhalation by the user, wherein the cumulative airflow is determined based on the measurements of airflow rate by the sensor. This allows the user control over the amount of vaporized liquid obtained in a given inhalation based on the cumulative airflow produced by the given inhalation.

It will be appreciated that the detailed nature of the control may vary from one implementation to another. For example, as described above, the control may be configured so that the cumulative vapor output, i.e. the overall (cumulative) amount of vaporized liquid for this inhalation, tracks the cumulative airflow through the device. Another possibility (for example) is that for a higher cumulative airflow, an additional heater element is activated. This may increase vapor output, or change the mix of vapor output, such as by altering the relative amounts of two different vapors in the vapor output.

The cumulative airflow represents the total volume of air that has passed into (through) the system so far, since the start of the inhalation. The start of the inhalation may be detected by the airflow sensor, which also then measures the current (instantaneous) airflow rate during the inhalation. The cumulative airflow can then be determined, for example, by integrating the measured current airflow from the start of the inhalation to the present stage of the inhalation. Another possible mechanism for determining the cumulative airflow is to measure the current or instantaneous airflow rate at multiple times, and then perform some modeling or lookup to determine the cumulative airflow. For example, the control of the vapor output may be based in part on a predicted airflow value—e.g. based on the cumulative airflow measured already for that particular inhalation and/or multiple instantaneous measurements of airflow, plus knowledge of a typical airflow rate variation with time (i.e. corresponding to line (a) in FIG. 7).

When additional measurements of the actual airflow are obtained, these can be compared with the predicted airflow rate, and any discrepancy used to adjust the future power supply to the heater. In some cases, the predicted airflow rate may be based on measured airflow rates for previous inhalations by that user. The use of a predicted airflow rate in this manner may help to improve the responsiveness of the control.

The cumulative airflow may be determined within the sensor itself, within the control unit, or within any other appropriate component of the electronic vapor provision system. The cumulative airflow may be determined explicitly or implicitly, using one or more other parameters that serve in effect as a proxy for the cumulative airflow. For example, the sensor may measure pressure drop, which may then be converted into a parameter that reflects the cumulative airflow (and hence can be used for controlling the power to the heater) without explicitly determining the cumulative airflow per se.

As described herein, a user can therefore control, at least in part, the vapor they receive. This control can be provided in an intuitive manner, e.g. just by puffing (inhaling) harder for more vapor, or by puffing softly for less vapor. The intuitive nature of the control is enhanced its rapid (real-time) responsiveness, in other words, if the user changes the puff (inhalation) rate during an individual puff, this produces a noticeable change in vapor output even during the same puff. For example, with reference to FIG. 7, we can see that the time responsiveness of the system is a small fraction of 1 s, typically less than 0.5 seconds, or less than 0.3 seconds, or less than 0.1 seconds. This time responsiveness represents the delay or time lag between a measured change in cumulative airflow and a corresponding change in vapor output, based on modifying the power supplied to the heater to reflect the current puff volume. (There is initial time lag of about 0.7 seconds in FIG. 7 for the cumulative vapor output to follow the cumulative airflow volume, but this represents the thermal inertia of the heater, rather than a time delay in the control loop). Accordingly, the linkage between puff volume and vapor output is readily apparent to the user, who is therefore able to learn quickly how to exploit this functionality of the device.

Furthermore, the approach described herein can be extended to a range of electronic vapor provision systems, such as heat-not-burn devices (which may include some plant matter or extract, for example, tobacco leaf, which is then heated or provided with steam to produce the desired vapor). One example of such an alternative form of electronic vapor provision system is described in US 2011/0226236, which discloses an inhaler containing an evaporator based on a composite planar structure that incorporates both a heating mechanism and wicking mechanism. Such a system provides high specific evaporative capacity for intermittent operation, combined with high evaporator (vaporizer) efficiency. Such a system may further include a pressure or airflow sensor for measuring airflow, and a control unit for controlling the power supplied to the heating mechanism in accordance with the approach described herein.

In order to address various issues and advance the art, this disclosure shows by way of illustration various embodiments in which the claimed invention(s) may be practiced. The advantages and features of the disclosure are of a representative sample of embodiments only, and are not exhaustive and/or exclusive. They are presented only to assist in understanding and to teach the claimed invention(s). It is to be understood that advantages, embodiments, examples, functions, features, structures, and/or other aspects of the disclosure are not to be considered limitations on the disclosure as defined by the claims or limitations on equivalents to the claims, and that other embodiments may be utilized and modifications may be made without departing from the scope of the claims. Various embodiments may suitably comprise, consist of, or consist essentially of, various combinations of the disclosed elements, components, features, parts, steps, means, etc other than those specifically described herein. The disclosure may include other inventions not presently claimed, but which may be claimed in future.

The invention claimed is:

1. An electronic vapor provision system including:
a vaporizer configured to vaporize liquid for inhalation by a user of the electronic vapor provision system;
a power supply comprising a cell or battery and configured to supply power to the vaporizer;
a sensor configured to measure the rate of airflow through the electronic vapor provision system as a result of a single inhalation by the user; and
a control unit configured to control the power supplied to the vaporizer for the single inhalation by the user, wherein during each iteration of time within the single inhalation the electronic vapor provision system is adapted to:
measure the current airflow rate at the sensor;
update a cumulative airflow by summing the measurements of current airflow rate by the sensor so far during all iterations of time within the single inhalation; and
control, by the control unit, the power supplied to the vaporizer based on the updated cumulative airflow for the most recent iteration of time within the single inhalation and a desired relationship between the cumulative airflow for the single inhalation and amount of vapor output to the user for the single inhalation;
thereby allowing the user control over the amount of vaporized liquid obtained in an individual single inhalation based on the cumulative airflow for that individual single inhalation.

2. The electronic vapor provision system of claim 1, wherein the vaporizer is a heater which is supplied with power from the power supply to heat and thereby vaporize the liquid for inhalation by a user based upon a signal provided by the controller.

3. The electronic vapor provision system of claim 2, wherein the control unit controls the power supplied to the heater to control the temperature of the heater.

4. The electronic vapor provision system of claim 1, wherein the liquid is nicotine.

5. The electronic vapor provision system of claim 1, wherein the sensor for measuring the rate of airflow measures a pressure drop, and the control unit estimates a measured airflow rate from the measured pressure drop.

6. The electronic vapor provision system of claim 1, wherein the control unit determines the cumulative airflow based on the measurements of airflow rate by the sensor.

7. The electronic vapor provision system of claim 1, wherein the control unit is configured so that a cumulative vapor output within the single inhalation is maintained approximately proportional to the cumulative airflow.

8. The electronic vapor provision system of claim 1, wherein the system controls the power supplied to the vaporizer based on
(i) the measured airflow rate $A(t)$,
(ii) the desired relationship between the cumulative airflow for the given inhalation and the amount of vaporized liquid provided to the user for the given inhalation, and
(iii) a system relationship between the power input to the vaporizer and the amount of vaporized liquid produced by the vaporizer.

9. The electronic vapor provision system of claim 1, wherein the system controls the power supplied to the vaporizer based at least on a predicted cumulative airflow, wherein the predicted cumulative airflow is derived from the measured rate of airflow for the given inhalation and a predetermined model for a puff profile.

10. The electronic vapor provision system of claim 1, wherein the system controls the power supplied to the vaporizer to provide the user with a real-time response in terms of amount of vapor output with respect to the cumulative airflow for the inhalation by the user.

11. The electronic vapor provision system of claim 10, wherein the system controls the power supplied to the vaporizer to provide the user with a real-time response of 0.3 seconds or less.

12. A method of operating an electronic vapor provision system including a vaporizer for vaporizing liquid for each of a series of single inhalations by a user of the electronic vapor provision system; a power supply comprising a cell or battery for supplying power to the vaporizer; a sensor and a control unit for iteratively controlling the power supplied to the vaporizer for each of the single inhalations by the user, said method comprising, for each iteration of time within each of the single inhalations:
measuring, by the sensor, the current airflow rate through the electronic vapor provision system as a result of the inhalation by the user;

updating a cumulative airflow by summing the measurements of current airflow rate by the sensor so far during the inhalation; and controlling, by the control unit, the power supplied to the vaporizer based on the updated cumulative airflow for this iteration and a desired relationship between the cumulative airflow for the inhalation by the user and amount of vapor output to the user for the corresponding single inhalation; thereby allowing the user control over the amount of vaporized liquid obtained in a given inhalation based on the cumulative airflow for the given inhalation.

13. The electronic vapor provision system of claim 1, wherein the desired relationship between the cumulative airflow for the single inhalation and amount of vapor output to the user for the single inhalation includes:

a first stage during which power to the vaporizer is set to 100%; and a second stage following the first stage, in which the controller is configured to power the vaporizer to provide an approximately constant proportion of vapor within the airflow.

14. The method of claim 12, further comprising controlling the power supplied to the vaporizer such that during a first stage the power to the vaporizer is set to 100%; and controlling the power supplied to the vaporizer such that during a second stage the power to the vaporizer is controlled to provide an approximately constant proportion of vapor within the airflow.

* * * * *